(12) United States Patent
Jang et al.

(10) Patent No.: US 12,128,154 B2
(45) Date of Patent: Oct. 29, 2024

(54) FILLER COMPRISING HYALURONIC ACID HYDROGEL HAVING EXCELLENT FILLING PROPERTIES

(71) Applicant: LG CHEM, LTD., Seoul (KR)

(72) Inventors: Cheol Jang, Daejeon (KR); Yeonsoo Kim, Daejeon (KR); Hyunsup Lee, Daejeon (KR); Myunghan Lee, Daejeon (KR); Ji Sun Kim, Daejeon (KR); Hyun Tae Jung, Daejeon (KR); Jineon So, Daejeon (KR); Chang Hyun Lee, Daejeon (KR); Hwayoun Ree, Daejeon (KR)

(73) Assignee: LG CHEM, LTD., Seoul (KR)

( * ) Notice: Subject to any disclaimer, the term of this patent is extended or adjusted under 35 U.S.C. 154(b) by 688 days.

(21) Appl. No.: 17/311,229

(22) PCT Filed: Dec. 19, 2019

(86) PCT No.: PCT/KR2019/018129
§ 371 (c)(1),
(2) Date: Jun. 4, 2021

(87) PCT Pub. No.: WO2020/130685
PCT Pub. Date: Jun. 25, 2020

(65) Prior Publication Data
US 2022/0016313 A1  Jan. 20, 2022

(30) Foreign Application Priority Data
Dec. 21, 2018 (KR) ................... 10-2018-0167782

(51) Int. Cl.
*A61L 27/20* (2006.01)
*A61K 31/167* (2006.01)
*A61L 27/52* (2006.01)

(52) U.S. Cl.
CPC ............ *A61L 27/20* (2013.01); *A61K 31/167* (2013.01); *A61L 27/52* (2013.01); *A61L 2300/204* (2013.01); *A61L 2300/402* (2013.01); *A61L 2400/06* (2013.01); *A61L 2430/34* (2013.01)

(58) Field of Classification Search
None
See application file for complete search history.

(56) References Cited

U.S. PATENT DOCUMENTS

| | | | |
|---|---|---|---|
| 4,582,865 A | 4/1986 | Balazs et al. | |
| 5,827,937 A | 10/1998 | Agerup | |
| 10,456,347 B2 | 10/2019 | Kim et al. | |
| 2005/0281880 A1 | 12/2005 | Wang | |
| 2013/0226235 A1 | 8/2013 | Fermanian et al. | |
| 2013/0244970 A1 | 9/2013 | Lebreton | |
| 2014/0039062 A1 | 2/2014 | Stroumpoulis et al. | |
| 2016/0144043 A1 | 5/2016 | Tauzin | |
| 2016/0228613 A1 | 8/2016 | Gavard Molliard | |
| 2018/0236129 A1 | 8/2018 | Roca Martinez et al. | |
| 2018/0344896 A1 | 12/2018 | Jung et al. | |
| 2021/0268143 A1 | 9/2021 | Jang et al. | |
| 2023/0211051 A1 | 7/2023 | Agerup | |

FOREIGN PATENT DOCUMENTS

| | | |
|---|---|---|
| BR | 112015031026 B1 | 7/2020 |
| CA | 2567532 C | 10/2013 |
| CN | 103285423 A | 9/2013 |
| CN | 104086788 A | 10/2014 |
| CN | 107223061 A | 9/2017 |
| EP | 2766056 B1 | 6/2017 |
| EP | 3804769 A1 | 4/2021 |
| ES | 2599329 T3 | 2/2017 |
| KR | 10-2012-0006451 A | 1/2012 |
| KR | 10-2015-0029578 A | 3/2015 |
| KR | 10-1660211 B1 | 9/2016 |
| KR | 10-1695564 B1 | 1/2017 |
| KR | 10-2017-0027090 A | 3/2017 |
| KR | 10-2017-0118105 A | 10/2017 |
| RU | 2671837 C2 | 11/2018 |
| TW | 201436827 A | 10/2014 |
| TW | 201709914 A | 3/2017 |
| WO | 2017-039030 A1 | 3/2017 |

OTHER PUBLICATIONS

Extended European Search Report dated Jan. 14, 2022, of the corresponding European Patent Application No. 19899340.4, 7 pages.
International Search Report and Written Opinion dated Apr. 10, 2020, issued in the corresponding International Application No. PCT/KR2019/018129, 11 pages.
Kim, et al., "Ex vivo magnetic resonance imaging using hyaluronic acid fillers: Differences between monophasic and biphasic fillers", Skin Res Technol., 2017, vol. 24, Issue. 1, pp. 16-19.
Didier, et al., "The Asymptotic Distribution of the Pathwise Mean Squared Displacement in Single Particle Tracking Experiments", J. Time Ser. Anal., 2017, vol. 38, Issue. 3, pp. 395-416.
Galadari, "Soft Tissue Augmentation Principles and Practice", ISBN 978-3-662-55844-7, Springer-Verlag GmbH Germany, 2018.

*Primary Examiner* — Layla D Berry
(74) *Attorney, Agent, or Firm* — ROTHWELL, FIGG, ERNST & MANBECK, P.C.

(57) ABSTRACT

The present invention has a special filling (WIE) property parameter value developed using microrheology technology, and thus exhibits improved high viscoelasticity flow properties, has low mobility when injected into skin whilst still maintaining the shape thereof, and thus has excellent soft tissue restoration properties, for example for the cheeks, breasts, nose, lips or bottom, and excellent volume expansion and wrinkle alleviation properties.

11 Claims, 4 Drawing Sheets

[Fig. 1]
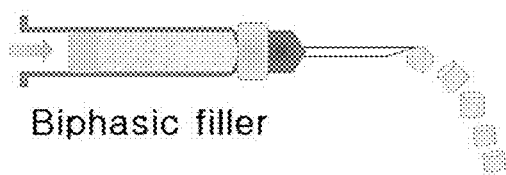
Biphasic filler
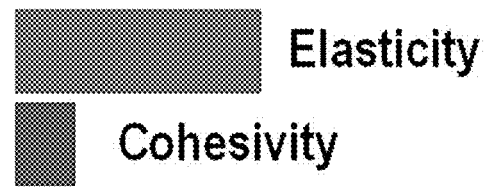
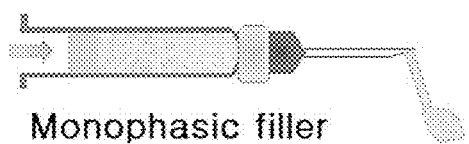
Monophasic filler
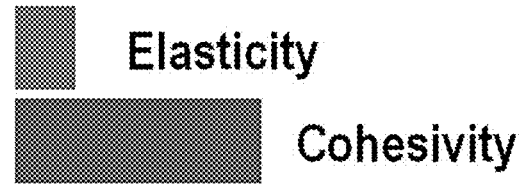
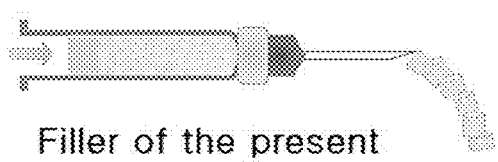
Filler of the present Invention
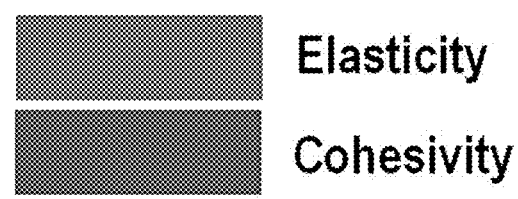

[Fig. 2]
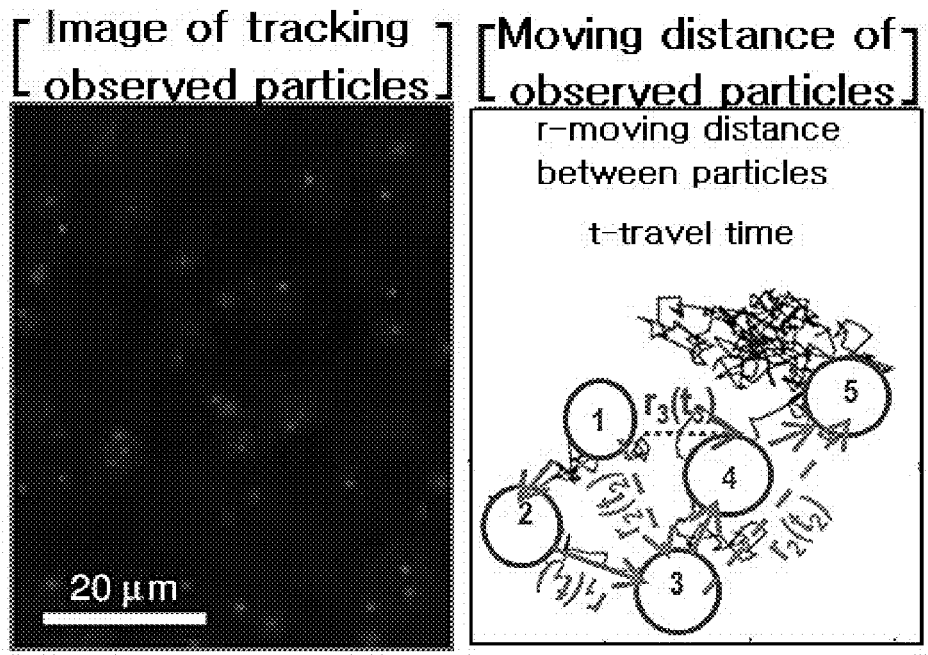
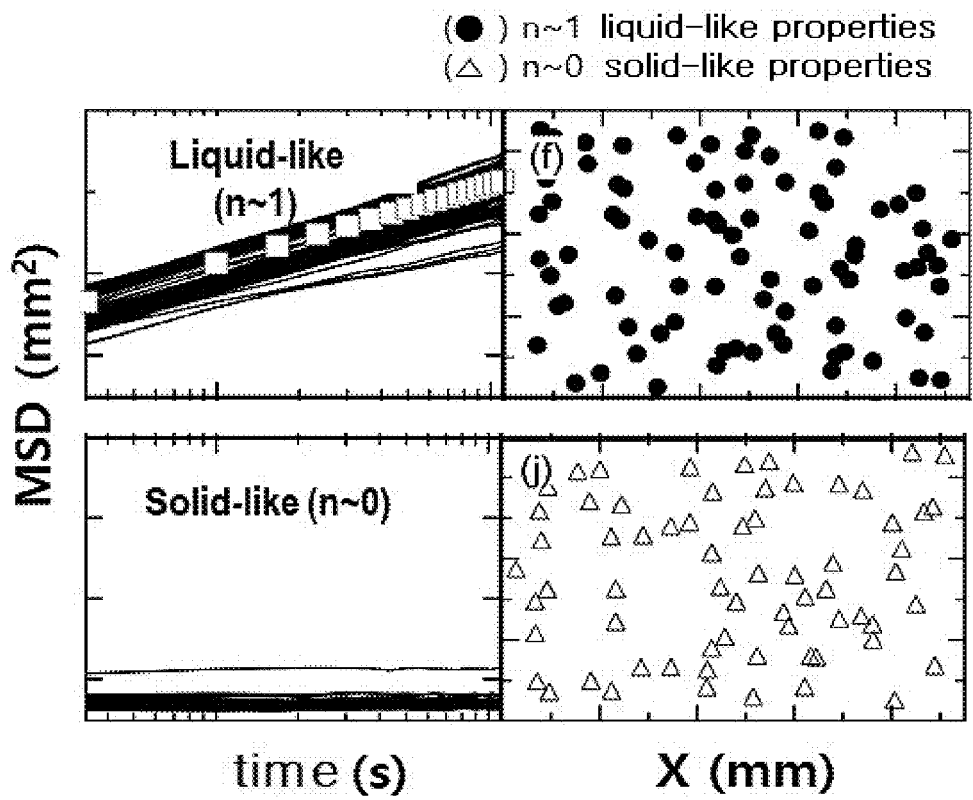

[Fig. 3]
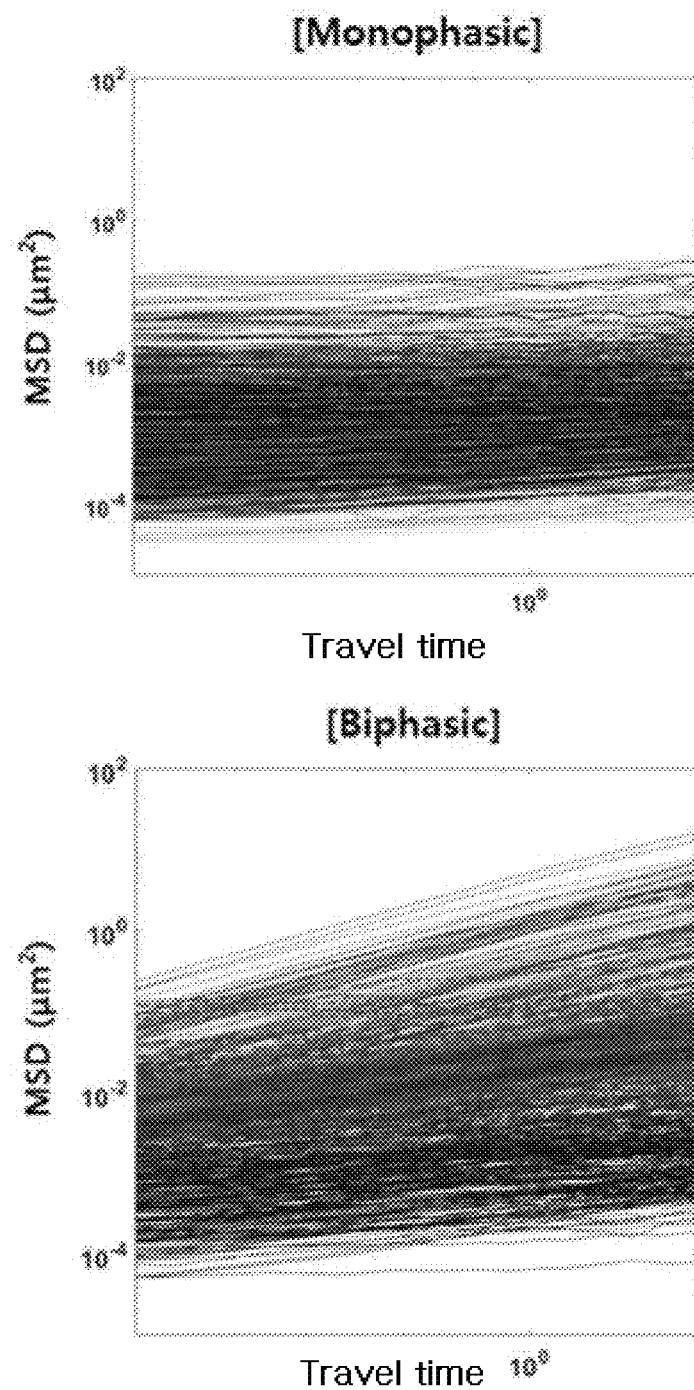

[Fig. 4]
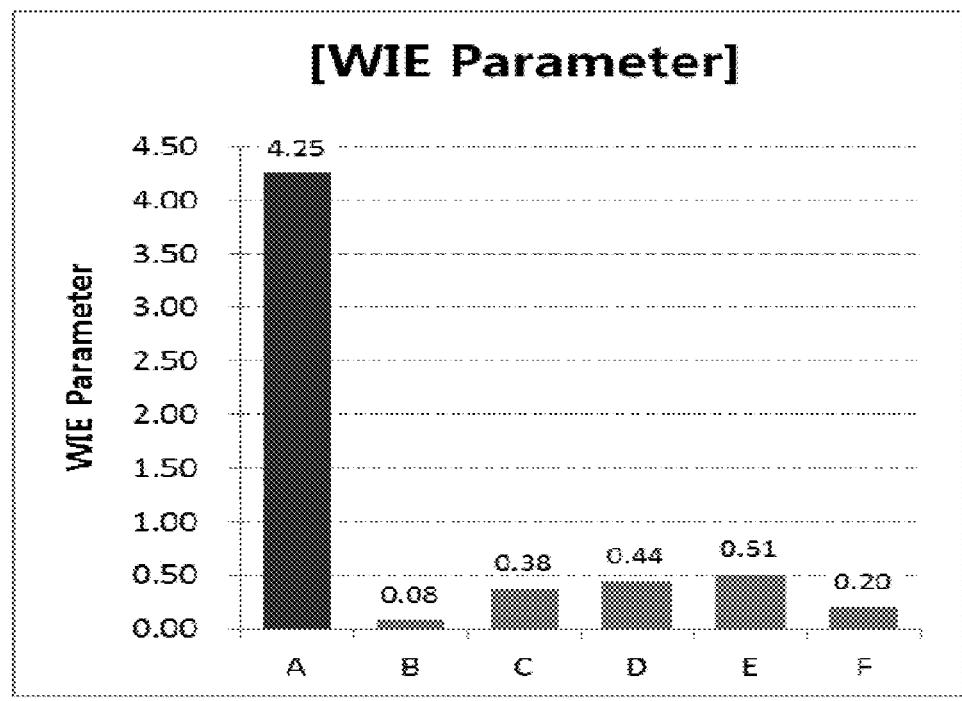

FILLER COMPRISING HYALURONIC ACID HYDROGEL HAVING EXCELLENT FILLING PROPERTIES

TECHNICAL FIELD

Cross-Reference to Related Application(s)

This application is a 35 U.S.C. 371 National Phase Entry Application from PCT/KR2019/018129, filed on Dec. 19, 2019 and designating the United States, which claims the benefit of priority based on Korean Patent Application No. 10-2018-0167782 filed on Dec. 21, 2018 with the Korean Intellectual Property Office, the full disclosures of which are incorporated herein by reference.

The present invention relates to a filler containing a hyaluronic acid hydrogel used for medical and cosmetic purposes, such as beauty care or tissue restoration. More particularly, the present invention relates to a filler which is suitable for a filler application, exhibits excellent phase properties and thus has excellent filling properties.

BACKGROUND OF THE INVENTION

The tissue of the human skin maintains its structure through an extracellular matrix containing proteins such as collagen or elastin, etc., and glycosaminoglycans. When a soft tissue defect occurs by external shock, diseases or aging or the like, tissue enhancement such as soft tissue enhancement has been used for medical and cosmetic purposes. Such enhancement has been made surgically via plastic surgery, or the shape has been restored and corrected in a non-surgical manner by injecting biological tissues or synthetic polymer chemicals into an affected site to increase and expand the volume of soft tissue. In this case, a material which is inserted as a component similar to a skin tissue into a specific site to augment soft tissue and thereby enlarge the volume of cheeks, lips, chest, hips, or the like for cosmetic purposes, and which is used for wrinkle improvement or contour correction by reducing fine wrinkles and deep wrinkles on the skin, is referred to as a material for soft tissue augmentation and also generally referred to as a dermal filler. The first-generation dermal filler developed for the first time in connection with these fillers includes products such as Zyderm and Zyplast produced by extracting animal-derived proteins, that is, animal proteins such as cows and pigs, and Cosmoderm or Cosmoplast produced using human collagen. However, it is rarely used for surgical operation in recent years because of a short duration of pharmaceutical effect and an inconvenience that a skin hypersensitivity test must perform one month before the operation.

The second-generation filer is hyaluronic acid (also referred to as 'HA') filler, which has a longer duration of effect than a collagen filler and is composed of N-acetyl-D-glucosamine and D-glucuronic acid, which are polysaccharides similar to the elements that make up the human body. Accordingly, it has the advantage that it has few side effects such as skin hypersensitivity reaction or the like, is easy to operate and remove, and can attract water to maintain skin moisture and also maintain the volume and elasticity and thus is suitable as a skin filler.

However, hyaluronic acid itself has a short half-life of only a few hours in the human body, and its application is limited, and therefore, studies have been conducted to increase the half-life (persistence in the body) of hyaluronic acid via crosslinking. For example, U.S. Pat. No. 4,582,865 discloses a crosslinked hyaluronic acid derivative using divinyl sulfone (DVS) as a crosslinking agent, and the hydrogel form thereof has been marketed under the trade name of Hylaform®. In addition, U.S. Pat. No. 5,827,937 discloses a method for preparing crosslinked hyaluronic acid derivatives by using a polyfunctional epoxy compound as a crosslinking agent, and among them, Restylane®, a crosslinked hyaluronic acid in the form of a hydrogel prepared using 1,4-butanediol diglycidyl ether (BDDE) (crosslinking agent) as a polyfunctional epoxy compound, is approved by the U.S Food and Drug Administration (FDA) and commercially available worldwide as a filler for tissue enhancement.

Such crosslinked hyaluronic acid hydrogel fillers exhibit unique phase properties by passing a crosslinked hyaluronic acid through a mesh with a size of several tens to several hundreds of micrometers or by subjecting it to a post-treatment process, and these are classified into two types according to the form of the phase. Specifically, these include fillers made of a single phase (monophasic HA filler) and fillers made of a bi-phase (biphasic HA filler).

Such crosslinked hyaluronic acid filler includes a filler made of a single phase (monophasic HA filler) and a filler made of a bi-phase (biphasic HA filler). Since monophasic hyaluronic acid filler is prepared using a homogeneous solution containing crosslinked hyaluronic acid, it has low elasticity and high cohesivity. Thus, when the monophasic hyaluronic acid filler is injected into the skin, it is unlikely to detach from the injected site, but has a problem that the injected shape cannot be maintained for a long time.

Biphasic hyaluronic acid hydrogel fillers are prepared from crosslinked hyaluronic acid particles alone or prepared by mixing with a non-crosslinked hyaluronic acid (non-treated, non-crosslinked hyaluronic acid, linear HA) similar to a liquid phase and passing through a mesh. Thus, they are divided into small grains in the form of particles, and generally have high elasticity and low cohesivity. Accordingly, when the biphasic hyaluronic acid hydrogel fillers are injected into the skin, the shape can be maintained for a long time, but there is a problem that the likelihood of detachment from the injected site is high. A typical example of such a biphasic HA filler is Restylane® (Galderma) mentioned above.

As such, each of the monophasic hyaluronic acid hydrogel fillers and the biphasic hyaluronic acid hydrogel fillers has advantages and disadvantages depending on the type. Therefore, it is necessary to appropriately select the type of filler depending on the treatment area and preference. However, there has been no proper evaluation tool capable of accurately evaluating the phase of the filler, and thus, there has been a difficulty in selecting and developing a high quality products.

BRIEF SUMMARY OF THE INVENTION

The present invention has been designed to solve the problems encountered in the prior art, and to provide a hyaluronic acid hydrogel having excellent filling properties, which are selected using microrheological parameters, a dermal filler containing the aforementioned hyaluronic acid hydrogel, and a biomaterial for tissue restoration containing the aforementioned hyaluronic acid hydrogel filler.

The present invention also provides a method for tissue restoration or wrinkle improvement using the aforementioned filler The present invention has been designed to solve the problems of the prior art, and a hyaluronic acid hydrogel exhibits excellent rheological properties such as viscoelasticity, cohesiveness, and regularity of filler structure when it has specific range of values of filling properties (WIE) parameter determined by using a mean rate of change of variable or a mean square displacement (MSD) distribution of tracer particles. Thus, it has been found that aforementioned hyaluronic acid hydrogel can be easily molded into a desired form when injected into soft tissues, for example, skin or the like, and can be stably maintained for a desired period of time, and thus, are excellent in filling properties, that is, properties for filler applications, for example, wrinkle improvement due to the filling of biological tissues and the filling of wrinkles, remodeling of the face or contouring, or restoration or increase in the volume of soft tissues, thereby completing the present invention.

One embodiment of the present invention is a hyaluronic acid-based hydrogel or a soft tissue filler containing the same, and relates to a hyaluronic acid hydrogel with excellent filling properties wherein a WIE parameter value derived by Equation 1 is 0.6 or more, a filler containing the aforementioned hyaluronic acid hydrogel, a prefilled syringe filled with the aforementioned filler, and a method for wrinkle improvement or tissue restoration including injecting the aforementioned filler.

Preferably, the filler is for soft tissue injection, for example, for skin injection, and the filler may be used as a filler having filling properties, for example, filling of biological tissues, wrinkle improvement by filling of wrinkles, and remodeling of the face or contour correction, or restoration or increase in the volume of soft tissue.

DETAILED DESCRIPTION OF THE INVENTION

Hereinafter, the present invention will be described in more detail.

The present invention relates to a hyaluronic acid hydrogel containing hyaluronic acid wherein a filling property (WIE) parameter has specific range of values, and a filler composition containing the same.

In the hyaluronic acid hydrogel according to the present invention or a filler containing the same, the "WIE (wrinkle improvement efficiency) parameter" is a parameter capable of reflecting elasticity, cohesivity and regularity of the filler structure, which are the major physical properties of the filler, and may be derived by Equation 1 below. The filler containing the hyaluronic acid hydrogel according to the present invention has a filling property in which a WIE parameter value is 0.6 or more, which satisfies the conditions of elasticity, cohesivity, and regularity of the filler structure.

WIE Parameter=([Average of MSD slope]*[Absolute value of MSD at travel time of 0.1 s]*[Standard deviation of MSD slope value]*100)$^{-1}$  [Equation 1]

in Equation 1, MSD refers to the mean squared displacement of tracer particles introduced into the filler containing the hyaluronic acid hydrogel.

The present invention analyzes the phase properties of the filler containing a hyaluronic acid hydrogel through microrheological techniques to provide a filler having excellent phase properties and filing properties derived therefrom. As used herein, the term "microrheological technique" is a technique for analogizing physical properties of a sample from the behavior of trace particles (e.g., polystyrene particles) dispersed in a small amount in the sample.

Specifically, the present invention uses the MSD of tracer particles to exhibit the phase properties and filling properties of the filler as measured according to such microrheological techniques. The MSD describes the microrheological parameters of the hyaluronic acid hydrogel, and uses a distribution of a mean square displacement (hereinafter, referred to as MSD) of a variable. The term "MSD" is a statistical parameter representing anomalous diffusion of particles, and means an average path variation of particles in a medium. The unit of MSD may be $\mu m^2$ or $mm^2$. When particles migrate freely due to Brownian motion (thermal fluctuation) in a general fluid, the MSD increases linearly with time, and the slope is given by the properties such as the viscosity and elasticity of the fluid. When the fluid is a pure viscous medium such as water, the MSD slope is 1, and when the fluid is a perfectly elastic medium such as a solid, it is 0. Further, when the fluid has properties that are intermediate between a liquid and a solid, it has an intermediate value of 0 and 1, and as the fluid is harder, it is closer to 0.

In the results of MSD analysis of tracer particles in the filler containing the hyaluronic acid hydrogel, the cohesivity of the hydrogel may be represented by the average of MSD slope, the elasticity by the absolute value of the MSD at a travel time of 0.1 seconds, and the regularity of the hydrogel by the standard deviation of the MSD slope, and the parameter considering all of these properties is the WIE parameter. When the WIE parameter is 0.6 or more, it can be determined to be a filler containing a hyaluronic acid hydrogel exhibiting desirable phase properties.

The filler containing the hyaluronic acid hydrogel according to the present invention exhibits excellent filling properties, and specifically, the WIE parameter may be 0.6 or more, preferably 0.6 or more to 20, or 1.0 to 20, more preferably 0.6 or more to 5 or less, or 1.0 or more to 5.0 or less.

Specifically, for the MSD measurement of tracer particles in the filler containing the hyaluronic acid hydrogel of the present invention, a test sample is prepared by dispersing the tracer particles, and the trajectory of the tracer particles moving in the filler is observed with an optical microscope, and then the observed image is analyzed by an image analysis program, and the mean square displacement according to the travel time of the tracer particles is measured. The tracer particles are particles dispersed in hyaluronic acid hydrogel for MSD analysis, and may be, for example, polymer particles, preferably polystyrene particles, and may be those having an average particle size of 0.5 to 2.0 µm. The measurement can be performed by adding 0.05 to 5% (v/v) of the tracer particles with respect to the sample to be analyzed, and the type, size and dispersion content of trace particles can be appropriately selected and used in consideration of the MSD analysis method and analysis device.

For example, it can be measured by a method in which the Brownian motion of the tracer particles dispersed in the test sample is photographed by using a video-microscopy, and then the movement of the particles is analyzed by using an image processing software (Matlab) or the like, which is illustrated in FIG. 2, but is not limited thereto.

The hyaluronic acid hydrogel according to the present invention has a feature that the absolute value of the MSD is 0.05 to 0.30, the average of the MSD slope is 0.05 to 0.20, and the standard deviation of the MSD slope is 0.10 to 0.21.

Specifically, when the MSD is measured, in the case of a filler having low cohesivity instead of high viscoelasticity, the movements of the tracer particles located on the surface region and the tracer particles located in the crosslinked region are different, and the tracer particles located on the surface region move relatively free, and thus exhibit a large MSD slope value, preferably, an MSD slope of greater than 0.8 to less than 1. In contrast, the tracer particles which have penetrated into the particles and located in the crosslinked region have a limited movement and thus have small MSD slope values, preferably greater than 0 to less than 0.5.

According to the present invention, the WIE parameter according to Equation 1 derived based on MSD shows a numerical value range of 0.6 or more, and as a result, it exhibits excellent properties as a filler, specifically, wrinkle-improving properties.

The wrinkle-improving property of the hyaluronic acid hydrogel filler according to the present invention may be represented by a lift capability (unit: Pa*N) calculated by the product of elasticity and cohesivity. The lift capability of the filler exhibits 600 or more, preferably 600 or more to 900 or less (Pa*N). When the WIE parameter according to the present invention exhibits a value of 0.6 or more, the lift capability exhibits 600 or more, preferably 600 or more to 900 or less (Pa*N), and the hyaluronic acid hydrogel filler exhibiting such WIE parameter has high cohesivity, viscoelasticity, and regularity and thus can exhibit excellent filling properties, that is, the filling of biological tissues, wrinkle improvement by filling of wrinkles, and remodeling of the face, or an effect of restoring or increasing the volume of soft tissues such as lips, nose, hips, cheeks or breasts.

As used herein, the "filling properties" of the hyaluronic acid hydrogel filler refer to properties that the hyaluronic acid hydrogel is suitable for performing its use as a filler, and may be represented by WIE parameter. Specifically, the filling properties may be, for example, properties such as wrinkle improvement due to the filling of biological tissues and the filling of wrinkles, remodeling of the face or contour correction, or restoration or increase in the volume of soft tissues.

As used herein, the "phase properties" of the hyaluronic acid hydrogel filler may be properties associated with the form of the hyaluronic acid hydrogel filler or physical properties resulting therefrom, and may be represented by microrheological parameters. The (visco)elasticity, cohesivity, regularity or the like which are the key qualities of the filler products, can be generally classified into monophasic and biphasic, depending on the phase of the filler.

The elasticity of the filler refers to the degree to which a desired shape is maintained under the skin tissue, and as the elasticity is higher, the original treated shape is maintained for a longer time. As used herein, the term "elasticity" refers to a property as a solid when a force is applied to an object, that is, a property in which the shape changes when a force is applied but returns to its original shape when the force is removed. The elasticity is represented by a storage elastic modulus (G'), and the unit is Pascal (Pa). In addition, as used herein, the term "viscosity" refers to exhibiting a property as a liquid, that is, a viscose flow which is a resistance to the flow. The viscosity can be represented by as a viscous modulus or loss modulus (G"), and the unit is Pascal (Pa). For example, elasticity is measured by determining how much stress is needed when a filler is loaded between the top and bottom of a circular geometry and a constant shear is applied thereto (shear strain=0.1%), the unit can be expressed in Pa, and the rate at which shear is applied can be expressed in 10 rad/s.

The cohesivity of a filler means that the filler particles are well aggregated. As used herein, the term "cohesivity" is an attractive force (adhesive force) acting between filler particles, which allows the filler particles to aggregate. As the cohesivity is higher, the force capable of supporting the tissue into the filler is injected is larger. In general, the cohesivity can be measured by a tack test or the like, and the cohesive force at the time of stretching at a constant speed after loading onto a rheometer is measured, and the unit is N (newton). For example, the cohesivity is measured as the force applied when the filler is loaded between the top and bottom of the geometry and pulled in a vertical direction. As the cohesivity between filler particles is larger, the greater force is needed to pull. The stretching speed was 1 mm/s and the unit is expressed in N.

In addition, the term "regularity" as used herein means how regularly the crosslinked structure of hyaluronic acid constituting the hyaluronic acid filler is formed, or when the hyaluronic acid filler is viewed as a lump, it means the degree of regularity between particles constituting the filler, or between particles and fluid.

In general, in the filler products, the elasticity and cohesivity are inversely related, but a filler having an excellent wrinkle-improving property is a filler excellent in both elasticity and cohesivity. Preferably, the filler containing the hyaluronic acid hydrogel according to the present invention has excellent filling properties satisfying all of the above properties.

In general, monophasic hyaluronic acid hydrogel fillers exhibit a cohesive gel form, has low elasticity but high cohesivity and thus show a high injection force. Examples thereof include Belotero® from Merz and Stylage® from Vivacy. In addition, biphasic hyaluronic acid particles have the feature that the elasticity is high and the cohesivity is low, and in order to exhibit such high elasticity, particles are produced with a large particle size. Examples thereof include Restylane® from Galderma. Therefore, the monophasic and biphasic hyaluronic acid hydrogel fillers previously known in the art are made difficult to satisfy all of the properties such as elasticity, cohesivity, and regularity of the filler structure.

In one embodiment of the present invention, the cohesivity, elasticity, and regularity of the filler structure of the hydrogel are analyzed using the microrheological parameters of the hyaluronic acid hydrogel filler, and the parameter considering all of these properties may be the WIE parameter. In Equation 1 which represents the WIE parameter, the average value of the MSD slope may describe the cohesivity of the hydrogel, the absolute value of the MSD at a travel time of 0.1 seconds may describe the elasticity of the hydrogel, and the standard deviation of the MSD slope may describe the regularity.

As used herein, the term "hyaluronic acid" is intended to include hyaluronic acid, a salt of hyaluronic acid, or a crosslinked body thereof.

The hyaluronic acid (hereinafter, also referred to as 'HA') of the present invention is a biopolymer material in which repeating units composed of N-acetyl-D-glucosamine and D-glucuronic acid are linearly connected, and the hyaluronic acid is often present in a vitreous humor of the eye, a synovial fluid of joints, rooster comb, and the like, and has excellent biocompatibility, and thus, has been widely used in the medical care and medical instrument fields such as ophthalmic surgical aids, joint function improvers, drug delivery materials, instillations, wrinkle improvers and the like, or in the cosmetics field. Specifically, the hyaluronic acid contained in the filler of the present invention may refer to a salt thereof in addition to hyaluronic acid.

The salt of hyaluronic acid includes, for example, both inorganic salts such as sodium hyaluronate, potassium hyaluronate, calcium hyaluronate, magnesium hyaluronate, zinc hyaluronate, cobalt hyaluronic acid, and the like, and organic salts such as hyaluronic acid tetrabutylammonium or the like, but is not limited thereto.

Further, preferably, the hyaluronic acid or a salt thereof may be crosslinked by a suitable crosslinking agent. The crosslinked hyaluronic acid derivative may be prepared by crosslinking the hyaluronic acid itself or a salt thereof using a crosslinking agent.

For the crosslinking of hyaluronic acid, a method of using a crosslinking agent in the presence of an aqueous alkaline solution may be used. The aqueous alkaline solution may be NaOH and KOH, preferably NaOH aqueous solution, but is not limited thereto. In this case, the NaOH aqueous solution may be used at a concentration of 0.1 to 0.5 N. The crosslinked hyaluronic acid contained in the filler of the present invention exhibits high viscoelasticity and cohesivity even when a low concentration and a small amount of crosslinking agent is used. The concentration of the crosslinking agent may be 1 to 10 mol %, preferably 1 to 5 mol %, relative to the mole of N-acetyl-D-glucosamine and D-glucuronic acid in the hyaluronic acid or a salt thereof.

The crosslinking agent may vary as a compound including two or more epoxy functional groups, and preferred examples thereof include 1,4-butanediol diglycidyl ether (BDDE), ethylene glycol diglycidyl ether (EGDGE), 1,6-hexanediol diglycidyl ether, propylene glycol diglycidyl ether, polypropylene glycol diglycidyl ether, polytetramethylene glycol diglycidyl ether, neopentyl glycol diglycidyl ether, polyglycerol polyglycidyl ether, diglycerol polyglycidyl ether, glycerol polyglycidyl ether, tri-methylpropane polyglycidyl ether, 1,2-(bis(2,3-epoxypropoxy)ethylene, pentaerythritol polyglycidyl ether, and sorbitol polyglycidyl ether. Among them, biepoxide-based 1,4-butanediol diglycidyl ether is particularly preferred in terms of having low toxicity.

In the present invention, the average molecular weight of the hyaluronic acid or the hyaluronic acid used in the crosslinking reaction may be 2,000,000 Da or more, 2,300,000 Da or more, or 2,500,000 Da or more, for example, 2,000,000 to 4,000,000 Da, 2,300,000 to 4,000,000 Da, 2,000,000 to 3,700,000 Da, 2,200,000 to 3,700,000 Da, or 2,500,000 to 3,500,000 Da.

In addition, the hyaluronic acid particles, preferably the crosslinked hyaluronic acid particles, in the filler containing the hyaluronic acid hydrogel according to the present invention may exhibit various shapes, but preferably, it may be a spherical shape. Further, the average diameter of such particles may be 10 to 1000 μm, 100 to 600 μm, 700 to 900 μm, 300 to 500 μm, or 300 to 400 μm.

In a preferred embodiment, in the filler containing the hydrogel according to the present invention, the hyaluronic acid, a salt thereof, or a crosslinked product thereof may be contained in an amount of 1 to 3% by weight based on the total weight of the filler.

The filler containing the hyaluronic acid hydrogel according to the present invention may further include not only hyaluronic acid but also water, an anesthetic agent, or a combination thereof.

The anesthetic agent include one or more types of anesthetic agents known in the art, preferably topical anesthetic agents, and the concentration of one or more anesthetic agent is in an amount effective to mitigate pain experienced upon injection of the composition. Examples of the anesthetic agent can be selected from the group consisting of ambucaine, amolanone, amylocaine, benoxinate, benzocaine, betoxycaine, biphenamine, bupivacaine, butacaine, butamben, butanilicaine, butethamine, butoxycaine, carticaine, chloroprocaine, cocaethylene, cocaine, cyclomethycaine, dibucaine, dimethisoquin, dimethocaine, diperodon, dycyclonine, ecgonidine, ecgonine, ethyl chloride, etidocaine, beta-eucaine, euprocin, fenalcomine, fomocaine, hexylcaine, hydroxytetracaine, isobutyl p-aminobenzoate, leucinocaine mesylate, levoxadrol, lidocaine, mepivacaine, meprylcaine, metabutoxycaine, methyl chloride, myrtecaine, naepaine, octocaine, orthocaine, oxethazaine, parethoxycaine, phenacaine, phenol, piperocaine, piridocaine, polidocanol, pramoxine, prilocaine, procaine, propanocaine, proparacaine, propipocaine, propoxycaine, pseudococaine, pyrrocaine, ropivacaine, salicyl alcohol, tetracaine, tolycaine, trimecaine, zolamine, and salts thereof. In one embodiment, the anesthetic agent may be lidocaine, for example, in the form of lidocaine hydrochloride.

The concentration of the anesthetic agent included in the filler may be about 0.1 to about 1.0% by weight, for example, about 0.2 to about 0.5% by weight, based on the total weight of the filler. The concentration of the anesthetic agent in the filler described herein can be therapeutically effective, which means that it is the concentration adequate to provide a therapeutic benefit in terms of convenience of surgical operation and patient compliance without inflicting harm to the patient.

The filler according to the present invention may further include a buffer solution, and a buffer solution may be used without limitation as long as it is used in the preparation of hyaluronic acid hydrogel. Preferred examples of such buffer solution include at least one buffer solution selected from the group consisting of citric acid, sodium hydrogen phosphate, sodium dihydrogen phosphate, acetic acid, diethyl barbituric acid, sodium acetate, tris(hydroxymethyl)methylamino)propanesulfonic acid) (TAPS), 2-bis(2-hydroxyethyl)amino) acetic acid (Bicine), tris(hydroxymethyl)amino methane (Tris), N-(2-hydroxy-1,1-bis (hydroxymethyl)ethyl)glycine (Tricine), 4-(2-hydroxyethyl)-1-piperazineethanesulfonic acid (HEPES), 2-[[1,3-dihydroxy-2-(hydroxymethyl)propan-2-yl]amino]methanesulfonic acid (TES), and piperazine-N,N'-bis(2-ethanesulfonic acid) (PIPES), but is not limited thereto. The content of the components included in the buffer solution may be appropriately adjusted, and may be preferably contained at a concentration of 0.3 to 2.0 g/L relative to the buffer solution.

The filler according to the present invention may further include an isotonic agent, and such an isotonic agent may be used without limitation as long as it is used for the preparation of hyaluronic acid hydrogel, and may be included in a buffer. As the preferred isotonic agent, sodium chloride may be used, but the isotonic agent is not limited thereto. The content of the isotonic agent may be appropriately adjusted as necessary, and may be contained in an amount of, for example, 7.0 to 9.0 g/L relative to the buffer, but is not limited thereto.

In one embodiment according to the present invention, a buffer containing sodium chloride, sodium hydrogen phosphate, and sodium dihydrogen phosphate in water for injection may be used.

In an additional aspect, the filler containing the hyaluronic acid hydrogel according to the present invention may further include acceptable components which can be included in the preparation of the filler, in addition to the aforementioned components.

Furthermore, the present invention is characterized in that the residual crosslinking agent is not substantially included in the filler containing the hyaluronic acid hydrogel having high filling properties, and the residual crosslinking agent is preferably contained in an amount of 0.5 ppm or less, which is the limit of detection.

The filler containing the hyaluronic acid hydrogel according to the present invention can be very effectively used for cosmetic or therapeutic purposes due to the filling properties having a WIE parameter of 0.6 or more.

As a specific example, the filler containing the hyaluronic acid hydrogel may be used for wrinkle improvement due to the filling of biological tissues and the filling of wrinkles, remodeling of the face, or restoring or increasing the volume of soft tissues such as lips, nose, hips, cheeks or breasts. The hyaluronic acid hydrogel filler may be administered in a dosage form suitable for such purposes, and may preferably be an injection.

Advantageous Effects

The filler containing hyaluronic acid hydrogel according to the present invention has a specific filling property parameter using the selection method thereof and thus can have an optimal filler effect.

BRIEF DESCRIPTION OF DRAWINGS

FIG. 1 is a diagram briefly showing the properties of the fillers having phase properties of the present invention, i.e., monophasic filler and biphasic filler.

FIG. 2 is a diagram illustrating the result of analyzing the motion of tracer particles using image processing software (Matlab).

FIG. 3 is a graph showing the MSD measurement results of the monophasic filler (Comparative Example 4) and biphasic filler (Comparative Example 1).

FIG. 4 is a graph confirming the parameters such as high cohesivity/high elasticity/regularity based on Equation 1 according to the present invention.

Hereinafter, the present invention will be described in more detail by way of Examples. However, these Examples are given for illustrative purposes only, and the scope of the invention is not limited to or by these Examples.

EXAMPLE 1: PREPARATION OF FILLER CONTAINING HYALURONIC ACID HYDROGEL

In order to prepare a filler containing the hyaluronic acid hydrogel according to the present invention, the following process was carried out.

More specifically, sodium hyaluronate having an average molecular weight of 2.5 to 3.5 MDa, sodium hydroxide, and 1,4-butanediol diglycidyl ether (BDDE) as a crosslinking agent were weighed. During the reaction, the concentration of sodium hyaluronate was 16 wt %, and the mol % of BDDE was 4% relative to the unit of sodium hyaluronate added. Separately, a sodium hydroxide (NaOH) aqueous solution at a concentration of 0.25 N was prepared and filtered. The weighed sodium hyaluronate, 0.25N sodium hydroxide aqueous solution, and 1,4-butanediol diglycidyl ether (BDDE) were put in a mixer tank and mixed homogeneously, and the mixer tank was placed in a constant temperature water bath and reacted overnight at a temperature of 30° C. to complete a crosslinking reaction. Thereafter, the crosslinked hyaluronic acid hydrogel after the reaction was roughly cut.

Meanwhile, salts and anesthetic agents were dissolved at a concentration of 1.26 g/L of sodium hydrogen phosphate hydrate (dodecahydrate), 0.46 g/L of sodium dihydrogen phosphate monohydrate (monohydrate), 7 g/L of sodium chloride and 3 g/L of lidocaine hydrochloride in a buffer tank containing water for injection to prepare a buffer solution. Some of the buffer solution was used as a primary buffer solution and transferred to a washing tank through a 0.22 µm filter. The cut hyaluronic acid hydrogel previously prepared was transferred to a washing tank containing a primary buffer solution and then stirred. The hyaluronic acid hydrogel was subjected to a primary washing and swollen, and then, when the swelling was completed, the washing solution was removed. Subsequently, the secondary buffer solution was transferred to a washing tank through a 0.22 µm filter and then stirred, and the hydrogel was subjected to a secondary washing and swollen, and then, when the washing and swelling were completed, the washing solution was removed. Thereafter, the tertiary buffer solution was transferred to a washing tank through a suitable 0.22 µm filter and then stirred, and the hyaluronic acid hydrogel was subjected to a third washing and swollen. Then, when the washing and swelling were completed, the washing solution was removed.

After completion of the third washing and swelling, it was confirmed whether the pH of the washing solution was in the neutral range, and after cutting the hyaluronic acid hydrogel gel in which washing and swelling was completed, it was transferred to an extruder tank to measure a weight, the buffer solution was added so that the weight of gel reaches a target weight, and a primary content correction was performed. When the primary content correction was completed, the hyaluronic acid hydrogel was extruded and ground in an extruder tank. Thereafter, the ground hyaluronic acid hydrogel was transferred to a sterilized tank and homogenized, after which the content was measured, and the buffer solution was added thereto to perform a secondary content correction. The hyaluronic acid hydrogel after the secondary content correction was heat-treated at a temperature of 121° C. or more for at least 1 minute, and degassing was performed by stirring the hyaluronic acid hydrogel under reduced pressure before loading into a syringe.

Thereafter, the hyaluronic acid hydrogel was vacuum-filled to each syringe by a predetermined amount and stoppered with a rubber stopper at the same time. The filled syringe was steam sterilized for at least 8 minutes at a temperature of 121° C. or higher in the final sterilizer.

EXPERIMENTAL EXAMPLE 1: MSD MEASUREMENT OF TRACER PARTICLES IN FILLER CONTAINING HYALURONIC ACID HYDROGEL USING MICRORHEOLOGICAL TECHNIQUE

For analyzing the properties of the prepared Example 1, the fillers containing commercial hyaluronic acid hydrogel of Comparative Examples 1 to 5 together with the hyaluronic acid hydrogel of Example 1 were used in the experiment, as shown in Table 1.

More specifically, the Brownian motion of the tracer particles dispersed in the sample was photographed using a video-microscope, and then the motion of the tracer particles was analyzed using an image processing software (Matlab) (FIG. 2).

Specifically, the test sample was prepared by dispersing 1 vol % of tracer particles (polystyrene particles having a diameter of 1 µm) in 1 mL of the filler of Example 1. Microrheological experiments were carried out by loading the filler sample in which the tracer particles were dispersed between transparent slide glasses, and recording the trajectory of the tracer particles moving into the filler through a camera connected to an optical microscope. The recording was performed 10 times for a minute each and averaged. The shooting speed was 38 frames per second. The recorded images were analyzed using an image analysis tool (Matlab), and how much the moving distance of the tracer particles changed with time, that is, the mean square displacement according to the travel time of the tracer particles, was plotted. In the same manner, the tracer particles were dispersed in the fillers containing the hyaluronic acid hydrogels of Comparative Examples 1 to 5 to prepare a test sample, and the behavior of the tracer particles was analyzed.

The characteristics of the mean square displacement (MSD) distribution of the tracer particles according to the phase properties of the hyaluronic acid hydrogel fillers were confirmed. Specifically, in the case of the biphasic filler of Comparative Example 1, the movements of the tracer particles located on the surface region and the tracer particles located in the crosslinked region were different, and the tracer particles located on the surface region had a relatively free movement, resulting in a large MSD slope value. In contrast, the particles which penetrated inside the particles and located in the crosslinked region had a limited movement, which exhibited a small MSD slope value. Meanwhile, the MSD distribution of the tracer particles for the monophasic filler of Comparative Example 4 was not divided into two regions, but showed similar slopes, thereby confirming that the particles formed a continuous shape without boundaries according to the region of the filler (FIG. 3). According to these results, it was confirmed that phase properties of the fillers could be inferred when the MSD value was measured by introducing the tracer particles into the fillers containing the hyaluronic acid hydrogel.

Furthermore, based on the relationship between the mean square displacement (MSD) slope value distribution of the tracer particles and the hydrogel phase, an attempt was conducted to derive parameters capable of reflecting the elasticity, cohesivity, and regularity of the filler structure, which are the most important physical properties of the filler for selecting excellent fillers.

Specifically, the tracer particles located on the surface region had a relatively free movement and thus exhibited a large value of MSD slope, and the tracer particles which penetrated into the filler and located in the crosslinked region had a limited movement and thus showed a small value of MSD slope. Accordingly, it was confirmed that these fillers had a large standard deviation of the MSD slope, and also shown that the average value of the MSD slope was large. In addition, it was confirmed that the absolute value of MSD at 0.1 seconds decreased as the elasticity increased. In contrast, in the case of fillers having low elasticity instead of high cohesivity such as monophasic fillers, the structure of the fillers was regular, and the standard deviation of the MSD slope value was small, and also, the tracer particles had a limited movement due to cohesivity, and thus showed a small MSD slope value.

Based on the results of the tests, as a parameter capable of reflecting the elasticity, cohesivity, and regularity of the filler structure of the filler, the "wrinkle improvement efficiency (WIE) parameter" represented by Equation 1 was devised.

$$\text{WIE Parameter} = ([\text{Average of MSD slope}] * [\text{Absolute value of MSD at travel time of 0.1 s}] * [\text{Standard deviation of MSD slope value}] * 100)^{-1} \quad [\text{Equation 1}]$$

In Equation 1, MSD represents the mean squared displacement of tracer particles. The cohesivity of the filler represents the average value of MSD slope, the elasticity represents the absolute value of MSD at travel time of 0.1 seconds for particles, and the regularity of the filler structure represents the standard deviation of the MSD slope value, and these properties were all considered.

Accordingly, it was confirmed that the physical properties of the hyaluronic acid fillers could be measured by the WIE parameter using MSD, and the WIE parameter values of the fillers of Example 1 and Comparative Examples 1 to 5 were confirmed according to Equation 1 reflecting all of the cohesivity, elasticity and the regularity of the filler structure of the filler, and the results are shown in Table 1 and FIG. 4 below.

TABLE 1

| Symbol | Sample | Average of MSD slope value | Absolute value of MSD at 0.1 s | Standard deviation of MSD slope value | WIE value |
|---|---|---|---|---|---|
| A | Example 1 | 0.120 | 0.109 | 0.180 | 4.25 |
| B | Comparative Example 1 (Restylane Lyft with Lidocaine) | 0.440 | 0.696 | 0.407 | 0.08 |
| C | Comparative Example 2 (Juvederm Voluma with Lidocaine) | 0.279 | 0.358 | 0.260 | 0.38 |
| D | Comparative Example 3 (Teosyal Puresense Ultimate with Lidocaine) | 0.255 | 0.416 | 0.214 | 0.44 |
| E | Comparative Example 4 (Teosyal Puresense Ultra Deep with Lidocaine) | 0.220 | 0.349 | 0.255 | 0.51 |
| F | Comparative Example 5 (Teosyal Puresense Deep Line with Lidocaine) | 0.420 | 0.507 | 0.236 | 0.2 |

In the case of the fillers having low cohesivity instead of high elasticity such as biphasic fillers, the structure of the fillers was not regular, and thus the movements of the tracer particles located on the surface region and the tracer particles located in the crosslinked region became different.

As shown in Table 1 and FIG. 4, the WIE parameter value of the filler according to Example 1 was 4.25, and the WIE parameter values of the fillers of Comparative Examples 1 to 5 were 0.51 or less. The fillers of Comparative Examples 1 to 5 had significantly lower WIE values compared to the filler of the Example according to the present invention, which did not satisfy the cohesivity, elasticity and regularity of the filler structure of the filler according to the present invention. In contrast, it was confirmed that the filler having a WIE parameter value of 0.6 or more could be selected as a filler having excellent filling properties (FIG. 4).

applied was 10 rad/s. The cohesivity was measured as the force applied when the filler was loaded between the top and bottom of the geometry and pulled vertically. As the cohesivity between filler particles was larger, the greater force was needed to pull. The stretching speed was 1 min/s, and the unit was expressed in N.

TABLE 2

| Example | Type | Cohesivity (N) | Storage Elastic Modulus (Pa) @10 rad/s | Lift capability | WIE Parameter |
|---|---|---|---|---|---|
| Example 1(A) | Both monophasic and biphasic | 1.414 | 620.72 | 878 | 4.25 |
| Comparative Example 1(B) | Biphasic | 0.590 | 598.264 | 353 | 0.08 |
| Comparative Example 2(C) | Monophasic | 0.815 | 296.604 | 242 | 0.38 |
| Comparative Example 3(D) | Monophasic | 1.346 | 391.664 | 527 | 0.44 |
| Comparative Example 4(E) | Monophasic | 1.634 | 354.452 | 579 | 0.51 |
| Comparative Example 5(F) | Monophasic | 1.186 | 235.074 | 279 | 0.20 |

Specifically, in Comparative Example 1, the regularity of the filler structure was confirmed to be poor because a standard deviation of the MSD slope value was large as a typical biphasic filler, and it was also confirmed that the cohesivity was low because the average value of the MSD slope was large. In Comparative Example 2, the elasticity of the filler was confirmed to be low because the absolute value of the MSD (value at 0.1 s) was large as a monophasic filler.

In the case of Example 1, it was confirmed that the absolute value of the MSD (value at 0.1 s) was low, the average value of the MSD slope was low, and the standard deviation of the MSD slope value was low, and the cohesivity, elasticity, and regularity of the filler were superior. Therefore, the filler of Example 1 shows an excellent form-keeping ability at the injection site, a low possibility of movement to other sites during surgical operation, and a regular structure of the filler, and thus is expected to show excellent filling properties.

EXPERIMENTAL EXAMPLE 2: CONFIRMATION OF WRINKLE-IMPROVING PROPERTY OF FILLER CONTAINING HYALURONIC ACID HYDROGEL

In order to confirm whether the WIE parameter of Experimental Example 1 is substantially associated with the wrinkle-improving property, the wrinkle-improving property of the hyaluronic acid fillers according to Example 1 and Comparative Examples 1 to 5 shown in Table 1 was measured according to the following method.

In order to measure the lift capability, which is a parameter showing the wrinkle-improving property, the elasticity and cohesivity of the fillers were measured by a rheometer (ARES-G2, TA Instruments), and the two values were multiplied to calculate the lift capability. The results of confirming such elasticity, cohesivity, and lift capability are shown in Table 2 and FIG. 4 below.

Specifically, the elasticity was measured by determining how much stress was needed when the filler was loaded between the top and bottom of the circular geometry and a constant shear was applied thereto (shear strain=0.1%), the unit was expressed in Pa, and the rate at which shear was From the results of the above Experimental Examples 1 and 2, it can be found that the filler containing the hyaluronic acid hydrogel according to the present invention exhibited a WIE parameter value of 4.25, which is greater than 0.6, and a high lift capability parameter, which is expressed as a product of elasticity and cohesivity, and represents the wrinkle-improving property, of 600 Pa*N or more, more preferably 800 Pa*N or more, and thus confirming that the filler of the present invention satisfied the elasticity and cohesivity at the same time. However, Comparative Examples 1 to 5, which are commercially available hyaluronic acid fillers, had a WIE parameter value of less than 0.6, did not show excellent elasticity and/or cohesivity, and had a lift capability of less than 600 Pa*N. Thus, it was confirmed that the wrinkle-improving property was not desirable as a filler compared to the filler of the present invention.

As a result, the filler (Example 1) having a WIE parameter value of 0.6 or more, as in the present invention, were excellent in cohesivity and elasticity, and exhibited a lift capability of 600 Pa*N or more, thereby being excellent in wrinkle-improving property.

The invention claimed is:
1. A filler comprising a hyaluronic acid hydrogel,
  wherein the hyaluronic acid hydrogel comprises a crosslinked hyaluronic acid obtained by crosslinking a hyaluronic acid having an average molecular weight of 2,000,000 Da to 4,000,000 Da, or a salt thereof with a crosslinking agent,
  wherein the crosslinked hyaluronic acid is contained in an amount of about 1% to about 3% by weight based on the total weight of the filler,
  wherein the hyaluronic acid hydrogel comprises the crosslinked hyaluronic acid particles with an average diameter of 300 to 500 μm, and wherein a wrinkle improvement efficiency (WIE) parameter in accordance with Equation 1 as a value for filling properties is 0.6 or more and 20 or less:

$$\text{Wrinkle Improvement Efficiency (WIE) Parameter} = ([\text{Average value of MSD slope}] * [\text{Absolute value of MSD at travel time of 0.1 s}] * [\text{Standard deviation of MSD slope value}] * 100)^{-1} \quad [\text{Equation 1}]$$

wherein in the Equation 1,

MSD refers to a mean square displacement for a plurality of tracer particles injected into the filler comprising a hyaluronic acid hydrogel at 1 vol %.

2. The filler of claim 1, wherein a value of an elasticity value times a cohesivity value is 600 or more and 900 or less Pa*N, wherein the elasticity value is a storage elastic modulus G' in Pascals (Pa) of the filler under a shear rate of 10 rad/s, and wherein the cohesivity value is a force in Newtons (N) when the filler is pulled vertically at a speed of 1 mm/s.

3. The filler of claim 1, wherein the filing properties comprise wrinkle improvement resulting from filling of biological tissues and wrinkles, remodeling of the face, or restoration or increase in the volume of soft tissues.

4. The filler of claim 1, wherein the crosslinked hyaluronic acid is prepared using a hyaluronic acid or a salt thereof and a crosslinking agent, wherein the crosslinking agent includes at least one crosslinking agent selected from the group consisting of 1,4-butanediol diglycidyl ether (BDDE), ethylene glycol diglycidyl ether (EGDGE), 1,6-hexanediol diglycidyl ether, propylene glycol diglycidyl ether, polypropylene glycol diglycidyl ether, polytetramethylene glycol diglycidyl ether, neopentyl glycol diglycidyl ether, polyglycerol polyglycidyl ether, diglycerol polyglycidyl ether, glycerol polyglycidyl ether, tri-methylpropane polyglycidyl ether, 1,2-(bis(2,3-epoxypropoxy)ethylene, pentaerythritol polyglycidyl ether, and sorbitol polyglycidyl ether.

5. The filler of claim 1, further comprising an anesthetic agent.

6. The filler of claim 5, wherein the anesthetic agent is lidocaine or a salt thereof.

7. The filler of claim 5, wherein the filler is for skin injection.

8. A prefilled syringe filled with the filler comprising a hyaluronic acid hydrogel of claim 1.

9. A biomaterial for tissue restoration comprising the filler comprising a hyaluronic acid hydrogel of claim 1.

10. A method for tissue restoration, comprising injecting to a subject the filler comprising a hyaluronic acid hydrogel of claim 1.

11. A method for wrinkle improvement, comprising injecting to a subject the filler comprising a hyaluronic acid hydrogel of claim 1.

* * * * *